US00PP10295P

United States Patent [19]

Wilkins

[11] Patent Number: Plant 10,295

[45] Date of Patent: Mar. 24, 1998

[54] YAUPON NAMED 'ORIENT JEWEL'

[76] Inventor: Curtis W. Wilkins, P.O. Box 143, Glen Flora, Tex. 77443

[21] Appl. No.: 745,457

[22] Filed: Nov. 12, 1996

[51] Int. Cl.[6] ..... A01H 5/00

[52] U.S. Cl. ..... Plt./65

[58] Field of Search ..... Plt./65

*Primary Examiner*—James R. Feyrer
*Assistant Examiner*—Elizabeth C. Kemmerer
*Attorney, Agent, or Firm*—Arnold, White & Durkee

[57] ABSTRACT

A new yaupon is described which is characterized by its lustrous dark green foliage, and extremely high branching density. The new tree is comparable in durability and resistance to temperature extremes to other varieties of *Ilex vomitoria* and has similar resistance to insect and disease. Tree size is also comparable to standard varieties; but the deep green densely borne foliage on numerous fine branches gives it a rich, full appearance that makes it attractive to the consumer and enhances commercial value.

2 Drawing Sheets

BACKGROUND OF THE NEW PLANT

The present invention relates to a new and distinct variety of a standard yaupon, *Ilex vomitoria*, which originated as a chance seedling in a cultivated area. The parents of the new yaupon variety are unknown. Several distinct and unusual characteristics distinguish the new plant from presently well known varieties such as *Ilex vomitoria* 'Pride of Houston', *Ilex vomitoria* 'Stokes' U.S. Plant Pat. No. 887, *Ilex vomitoria* 'Shillings' and *Ilex vomitoria* 'Pendula'. The inventor observed the tree growing uncharacteristically in a nursery environment in Louisiana and took particular note of the distinctions between it and other standard yaupon *Ilex vomitoria*.

Asexual reproduction of the new variety by vegetative softwood cuttings on the inventor's farm in Glen Flora, Tex., has shown that the new characteristics are permanently fixed through successive propagations.

'Orient Jewel' is an attractive, small, multi-trunked bush-formed tree, which is prominently distinguished by its extremely small dark lustrous leaves and short internode length. The new plant has endured the same growing conditions in Southeast Texas during 1989 to 1996 as standard varieties of *Ilex vomitoria*. It exhibits the same durability to temperature extremes and adverse conditions as *I. vomitoria*. It appears to be no more susceptible to insects and disease than any other variety of *I. vomitoria*. 'Orient Jewel' has been established to be moderately easy to asexually propagate by means of stem cuttings which root with about 90% take. The bud stem and foliage traits of the clones appeared to be identical to the parent, 'Orient Jewel'.

The following characteristics distinguish the new yaupon from other *Ilex vomitoria* commercially known and used in the nursery industry.

The following table summarizes some of the differences between 'Orient Jewel', 'Pride of Houston' and Dwarf Yaupons.

TABLE 1

| | 'PRIDE OF HOUSTON' | DWARF | 'ORIENT JEWEL' |
|---|---|---|---|
| Height at 5 Years | 2.3 m | 0.6 m | 2.3 m |
| # Lateral Branches Per Meter of Trunk | 53 | 91 (EST.) | 128 |
| Avg. Length of Lateral Branches | 18–46 cm | 9–18 cm | 7.5–18 cm |

TABLE 1-continued

| | 'PRIDE OF HOUSTON' | DWARF | 'ORIENT JEWEL' |
|---|---|---|---|
| Leaf Size (cm × cm) | 2.1 × 1.0 | 2.0 × 0.8 | 0.5 × 0.35 |
| Leaf Color | dark green | dark grey green | black green |

DESCRIPTION OF THE DRAWINGS

Photograph 1 shows a comparison of the branches of 'Orient Jewel' on the left and a standard yaupon, *I. vomitoria* 'Pride of Houston' on the right depicting the smaller, darker green leaves and the shorter internode length of 'Orient Jewel'.

Photograph 2 depicts a full side view of a 5 year old 'Orient Jewel' specimen tree currently in production in a fifteen gallon plastic container.

DESCRIPTION OF THE NEW VARIETY

Branching and growth habits: The evergreen variety has extremely high branching density caused by densely borne foliage that occurs on the many fine branches. The tree appears to be standard in size when compared to standard *I. vomitoria* in current production.

Height: The new tree is 2.1 to 2.6 m in height, 1.5 to 1.6 m in spread with a multi-trunk characteristic of 2.5 to 4.0 cm in caliper per cane.

Branching: Main branches generally are 40 to 91 cm in length and the branches are 4 to 10 cm in length at maturity. Branching is alternate with typical branch angles ranging from 50 to 60 degrees.

Internode length: A distinguishing chracteristics, the internode length, is 0.6 cm to 1.0 cm.

Resistance to insects and disease: This tree has shown no more resistance or susceptibility to diseases and insects that normally infest standard yaupon, *Ilex vomitoria*. The two have been grown side by side and received the same preventive sprays for the last seven years in a nursery environment.

Leaves: Alternate, simple, 0.4 to 0.6 cm long, 0.3 to 0.4 cm wide, acute to obtuse apex, acute to rounded base, lustrous dark green, almost black green above, gray green beneath, leathery, undulate to crenate with pinnate venation, glabrous above and beneath, petiole, 0.1 cm in length, light green and glabrous.

Stem: Gray brown in color, fine textured, glabrous.

Flowers: To date this tree has not demonstrated any flowers.

Fruit: None observed.

Propagation: Softwood cuttings have been taken from the parent seedling and subsequent generations for the past seven years. Cuttings were stripped of basal foliage, dipped in 0.8 kiba solution, placed in a 100% pine bark medium under intermitten mist. 80–90% rooting has been consistent from year to year.

What is claimed is:

1. A new and distinct variety of *Ilex vomitoria* as herein described and illustrated, primarily distinguished by its leaf size, and leathery lustrous black green foliage.

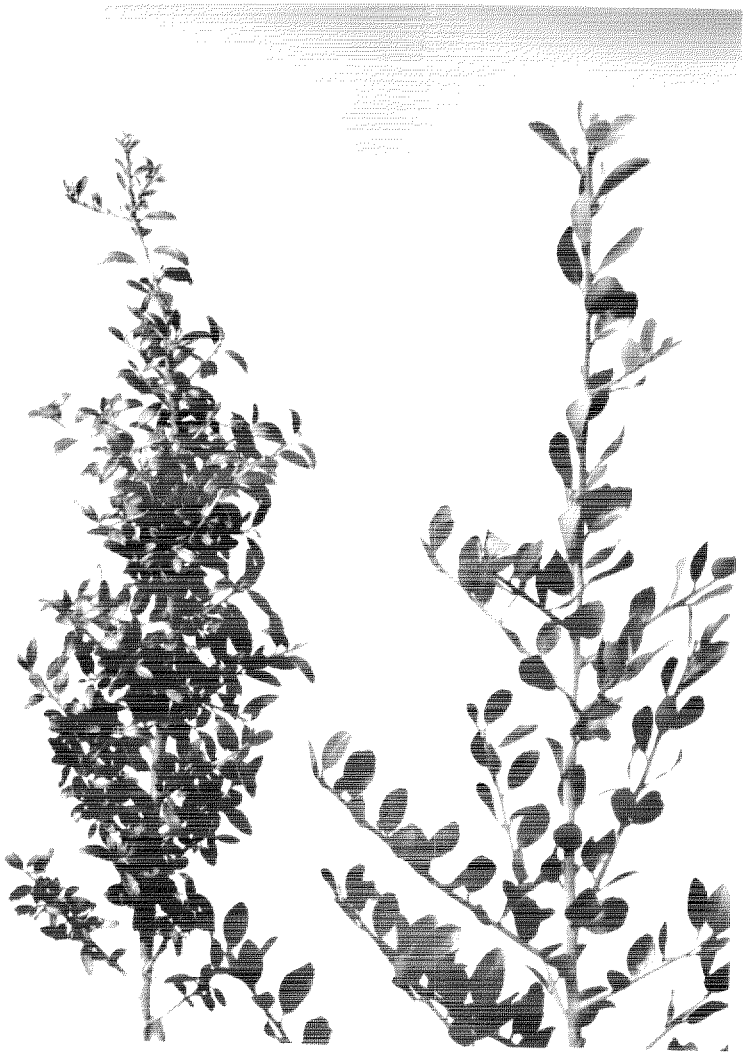

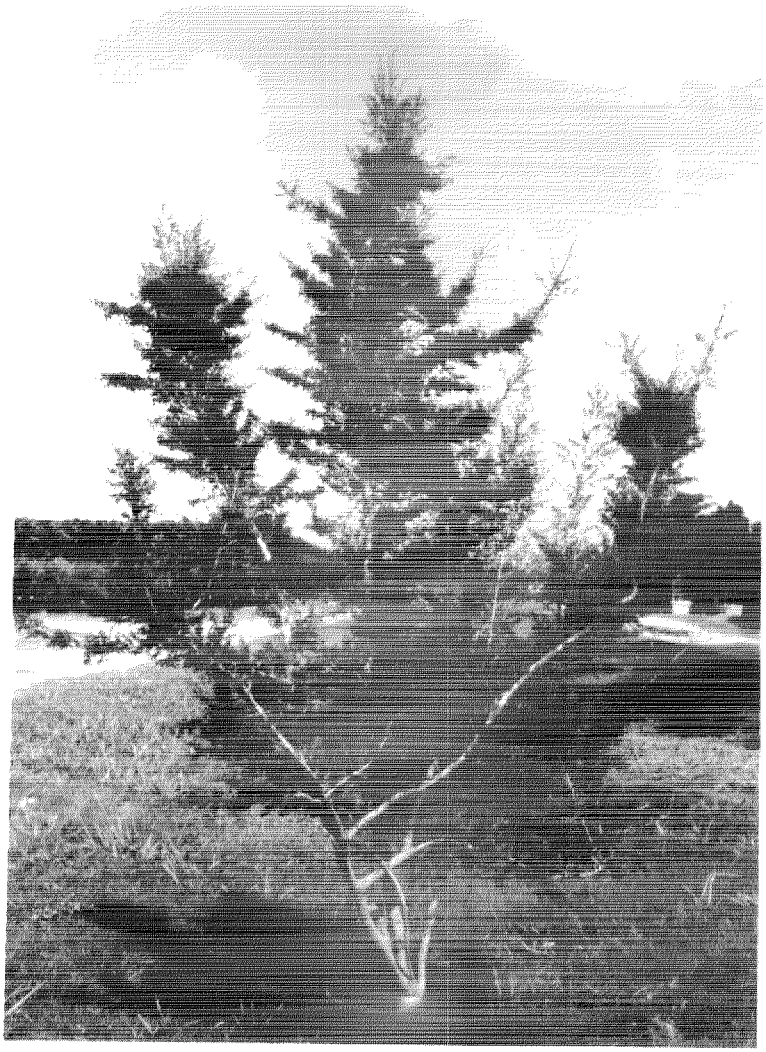

* * * * *